(12) United States Patent
Hartley et al.

(10) Patent No.: US 7,008,056 B2
(45) Date of Patent: Mar. 7, 2006

(54) EYEWEAR FOR BALLISTIC AND LIGHT PROTECTION

(75) Inventors: Scott M. Hartley, Clarks Summit, PA (US); Robert A. Sallavanti, Dalton, PA (US); Brad Sutter, Exeter, PA (US)

(73) Assignee: Gentex Corporation, Carbondale, PA (US)

( * ) Notice: Subject to any disclaimer, the term of this patent is extended or adjusted under 35 U.S.C. 154(b) by 0 days.

(21) Appl. No.: 11/187,500

(22) Filed: Jul. 22, 2005

(65) Prior Publication Data

US 2005/0264753 A1     Dec. 1, 2005

Related U.S. Application Data

(63) Continuation of application No. 10/215,717, filed on Aug. 9, 2002, now Pat. No. 6,923,537.

(51) Int. Cl.
*G02C 7/10*     (2006.01)

(52) U.S. Cl. .................... 351/44; 351/163; 351/166

(58) Field of Classification Search .............. 351/41, 351/44, 49, 159, 163, 166; 349/13, 14; 359/14, 359/15

See application file for complete search history.

(56) References Cited

U.S. PATENT DOCUMENTS

| | | | |
|---|---|---|---|
| 4,601,533 A | | 7/1986 | Moss |
| 4,637,678 A | * | 1/1987 | Moss et al. .................. 359/15 |
| 4,802,719 A | | 2/1989 | Magarinos et al. |
| 4,810,080 A | | 3/1989 | Grendol et al. |
| 4,830,441 A | | 5/1989 | Chang |
| 4,978,182 A | | 12/1990 | Tedesco |
| 5,103,323 A | | 4/1992 | Magarinos et al. |
| 5,173,811 A | | 12/1992 | Gumbs |
| 5,373,392 A | | 12/1994 | Bala |
| 5,432,623 A | | 7/1995 | Egan et al. |
| 5,539,544 A | | 7/1996 | Le Paih et al. |
| 5,604,547 A | | 2/1997 | Davis et al. |
| 5,751,473 A | | 5/1998 | Runciman |
| 5,790,230 A | | 8/1998 | Sved |
| 5,802,622 A | | 9/1998 | Baharad et al. |
| 5,929,963 A | | 7/1999 | McNeal |
| 5,942,716 A | | 8/1999 | Miller |
| 5,995,280 A | | 11/1999 | Beach |
| 6,196,678 B1 | | 3/2001 | Chapin, III |
| 6,231,183 B1 | * | 5/2001 | Dillon .................. 351/163 |
| 6,291,070 B1 | | 9/2001 | Arpac et al. |

(Continued)

FOREIGN PATENT DOCUMENTS

EP     0 331 469     9/1989

(Continued)

OTHER PUBLICATIONS

James M. Tedesco; Holographic Laser-protective Filters and Eyewear, Optical Engineering; Jun. 1989; pp. 609-615; vol. 28. No. 6.

(Continued)

*Primary Examiner*—Huy Mai
(74) *Attorney, Agent, or Firm*—Keusey, Tutunjian & Bitetto, P.C.

(57) ABSTRACT

The present invention provides eye protection systems. The eye protection systems include a lens capable of being mounted in and being interchangeable between a plurality of different lens-mounting platforms. These platforms may include spectacles or goggles with release mechanisms, which permit the lens to be removed while providing full ballistic protection when installed in the platform. The lens of the present invention protects against a plurality of threats including spectrums of light, such as sun light, ultraviolet light, or laser light, wind, dust, projectiles, etc. The lens may include a laminate structure, which protects sensitive technologies from exposure to environmental conditions, such as chemicals, weather, etc.

21 Claims, 12 Drawing Sheets

U.S. PATENT DOCUMENTS

| | | |
|---|---|---|
| 6,316,084 B1 | 11/2001 | Claus et al. |
| 6,318,859 B1 | 11/2001 | Baudart et al. |
| 6,343,860 B1 | 2/2002 | Pierotti |
| 6,355,124 B1 | 3/2002 | Blomberg et al. |
| 6,364,481 B1 | 4/2002 | O'Connor et al. |
| 6,382,789 B1 | 5/2002 | Baudart et al. |
| 6,404,106 B1 | 6/2002 | Dale et al. |
| 6,414,794 B1 | 7/2002 | Rosenthal |
| 6,637,877 B1 | 10/2003 | Hartley et al. |
| 2004/0070726 A1 * | 4/2004 | Ishak .......................... 351/163 |

FOREIGN PATENT DOCUMENTS

FR          2 765 696          1/1999

OTHER PUBLICATIONS

CRUFFLER.COM presents Accessory Review, Jul. 2001; pp. 1-7; http://www.cruffler.com/accessory.review-july-01.html.

Maj. Kent Harrington; Laser Eye Protection; pp. 1-3; http://www.brooks.af.mil/AFRL/HED/HEDO/lep..htm.

Goggles & Eyewear, on-line catalog; http://www.specwargear.com/goggle-1.html.

The Tactical Retail Corporation; on-line catalog; http://www.tacticalshop.com/police_tactical/catalog214_0.html; pp. 1-2.

Ray Linville; Laser Protective Eyewear (LPE); p. 1-2; http://www.dtic.mil/dpatitle3/lpe.htm.

* cited by examiner

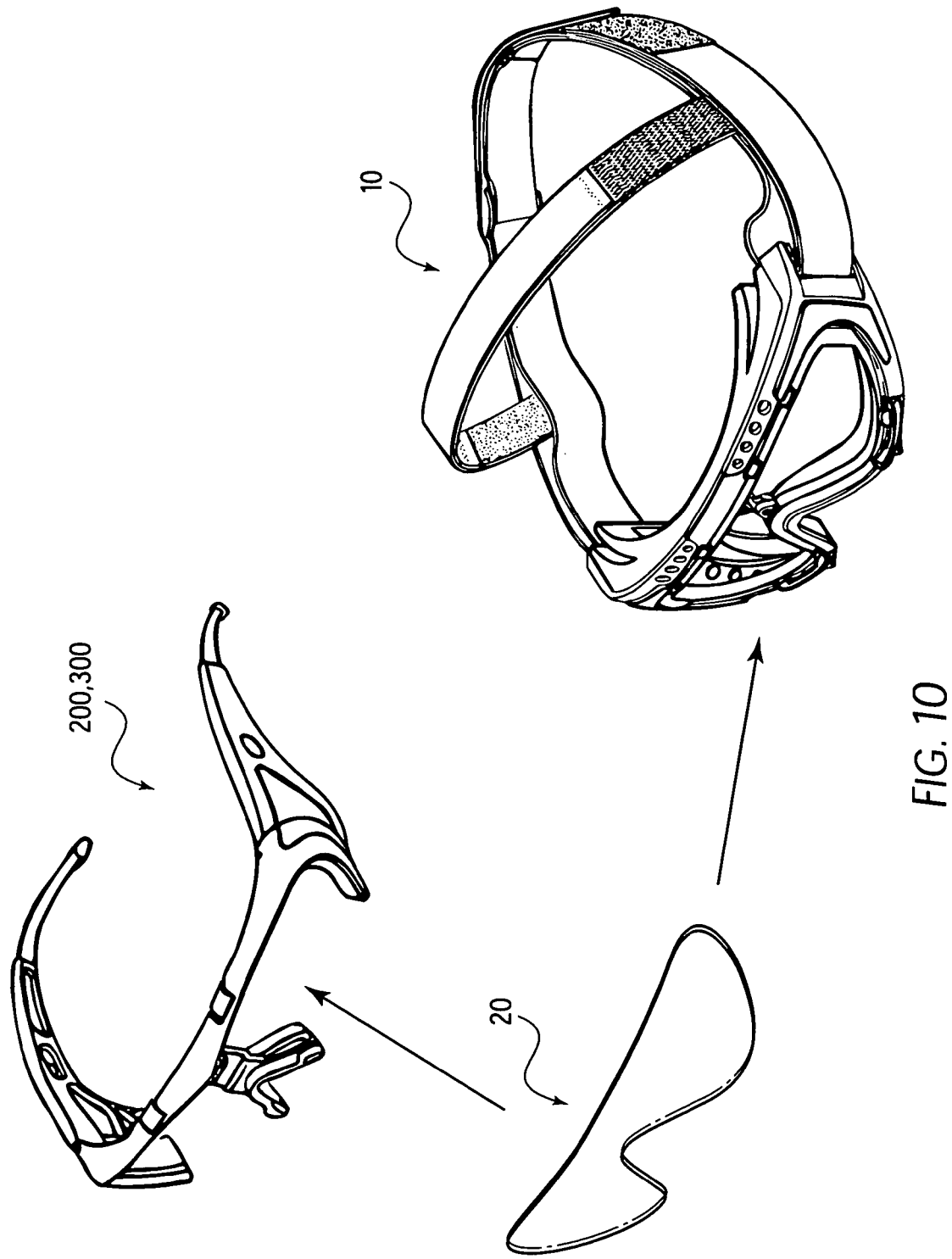

EYEWEAR FOR BALLISTIC AND LIGHT PROTECTION

CROSS REFERENCE TO RELATED APPLICATIONS

This application is a continuation of application Ser. No. 10/215,717 filed on Aug. 9, 2002, now U.S. Pat. No. 6,923,537.

BACKGROUND OF THE INVENTION

1. Field of the Invention

The present invention relates to protective eyewear and more particularly to a multiple threat eye protection system, which includes an easily removable lens that is transferable between multiple lens-retaining platforms.

2. Description of the Related Art

Eye protection systems have a plurality of applications. Eye protection systems may be employed as sports equipment, e.g., ski goggles, as protection for work activities, as protection for military applications or many other applications. Typical eye protection systems include a zero-power plano lens, which is employed for wind, dust and debris protection, whereas military eye protection systems typically require additional protection from threats such as high speed ballistics and ultra-violet light. While these lenses may be removed, they often require tools and the disassembly of multiple parts to do so. It would be advantageous to provide a lens, which is easily removable without the use of tools from one or more retaining platforms, such as a goggle or spectacle.

Eye protection can be provided on a plurality of different platforms. For example, goggles protect against dust and wind while spectacles are preferred for sunlight protection. Each of these platforms is constrained by different requirements and different physical attributes. For example, goggles tend to sit further from the face of a user than spectacles. Additional differences between these platforms include the pantoscopic tilt angle of the lens relative to the face of the user and the overall size of the lens to provide proper coverage of the user's eyes.

The production of military eyewear tends to be material and time intensive. In particular, lens designs which include protection from multiple threats typically undergo many processing steps, which affect their yield and therefore cost. It would be advantageous to provide a lens system, which is interchangeable between different lens retaining platforms, which addresses the difficulties in employing the same lens for multiple platforms. Such a lens system would reduce cost by permitting a single lens to be employed on several platforms.

Lenses for military applications typically include coatings or layers formed thereon. Despite providing ballistic protection, these lenses cannot in many cases provide adequate scratch resistance, and light protection layers are vulnerable to scratches and, if scratched, may compromise their light protection effectiveness. For example, where laser or other light protection is provided, scratches in the protective coating could render the lens useless for light protection applications. The lens must therefore be replaced. It would be advantageous to improve scratch resistance of the lenses, which are designed to protect against light threats, e.g., laser light.

Therefore a need exists for lens retaining platforms, which provide an easy and quick release mechanism for removing a lens and accommodate lenses of different thicknesses and which can be interchanged between the platforms. A further need exists for a lens system, which protects against multiple threats and provides a structure, which protects optical technologies from scratch or other damage.

SUMMARY OF THE INVENTION

The present invention provides eye protection systems. The eye protection systems include a lens capable of being mounted in and being interchangeable between a plurality of different lens-mounting platforms. These platforms may include spectacles or goggles with release mechanisms, which permit the lens to be removed while providing full ballistic protection when installed in the platform. The lens of the present invention protects against a plurality of threats including spectrums of light, such as sun light, ultraviolet light, or laser light, wind, dust, projectiles, etc. The lens may include a laminate structure, which protects sensitive technologies from exposure to environmental conditions, such as chemicals, weather, etc.

The present invention includes an eye protection system having a lens for protecting both eyes of a user. The lens is interchangeable between multiple platforms. The platforms include at least one of a goggles assembly and a spectacles assembly, which detachably receive the lens and hold the lens in a position on a face of the user by securing the lens about its periphery.

In another embodiment, an eye protection system includes a frame having a recess formed therein, and an elastomeric subframe attached to the frame and lining surfaces of the recess. The recess is configured to receive a lens such that the lens, when installed, remains in contact with the subframe. Tabs are disposed at a periphery of the recess on a first side of the frame to provide a gap between the subframe and the tab, which permit the lens to fit in the gap. A release mechanism is disposed at a periphery of the recess on a second side opposite the first side of the frame. The release mechanism secures the lens when placed in a first position.

In another embodiment, the eye protection system includes a unitary lens having two lobes and a centrally disposed arch adapted for a nose of a user. A brow bar has opposing extensions extending therefrom, the extensions capture a portion of the lens, which opposes the brow bar. A support portion is included for capturing the lens, and the support portion is detachably connected to the arch of the lens and extends over the brow bar to secure the lens to the brow bar. Arms are pivotally connected to the brow bar for securing the lens on a user.

The present invention includes a lens system for protection against light and ballistics, which includes a first lens having a convex surface. A hologram is adhered to the convex surface. A second lens includes a concave surface. A dielectric stack is formed on the concave surface. An index-matching adhesive is provided for connecting the convex surface with the hologram to the concave surface with the dielectric stack.

Other lens-retaining platforms and lens structures are contemplated by the present invention. The illustrative embodiments of the present invention should not be construed as limiting the present invention as presented in the appended claims.

BRIEF DESCRIPTION OF THE DRAWINGS

The advantages, nature, and various additional features of the invention will appear more fully upon consideration of the illustrative embodiments now to be described in detail in connection with accompanying drawings. In the drawings wherein like reference numeral denote similar components throughout the views:

FIG. 10 is a schematic perspective view showing a lens system having the capability of being interchangeable between goggles and spectacles in accordance with the present invention.

DETAILED DESCRIPTION OF PREFERRED EMBODIMENTS

The present invention provides an eye protection system, preferably a military eye protection system, which provides a lens, which is interchangeable between lens-retaining platforms. For example, a lens may be employed with a goggles system, then removed from the goggle system and inserted into a spectacle system. The present invention features custom designed quick release mechanisms on each lens-retaining platform, which make the lens easily removable and installable without the use of tools. The lens-retaining platforms of the present invention provide for anthropometric adjustments to individual users. The lens systems of the present invention provide the capability to easily replace the lenses. Prior art systems required time (e.g., about 10 minutes), tools (e.g., a screwdriver) and manual dexterity to replace the lens. The present invention provides the capability of easily removing and replacing lenses. In addition, the lenses of the present invention are interchangeable between different lens mounting platforms. Despite the removeablity and interchangeability of the lenses of the present invention, each lens provides full ballistic protection when properly installed on the various platforms.

Figure 1:
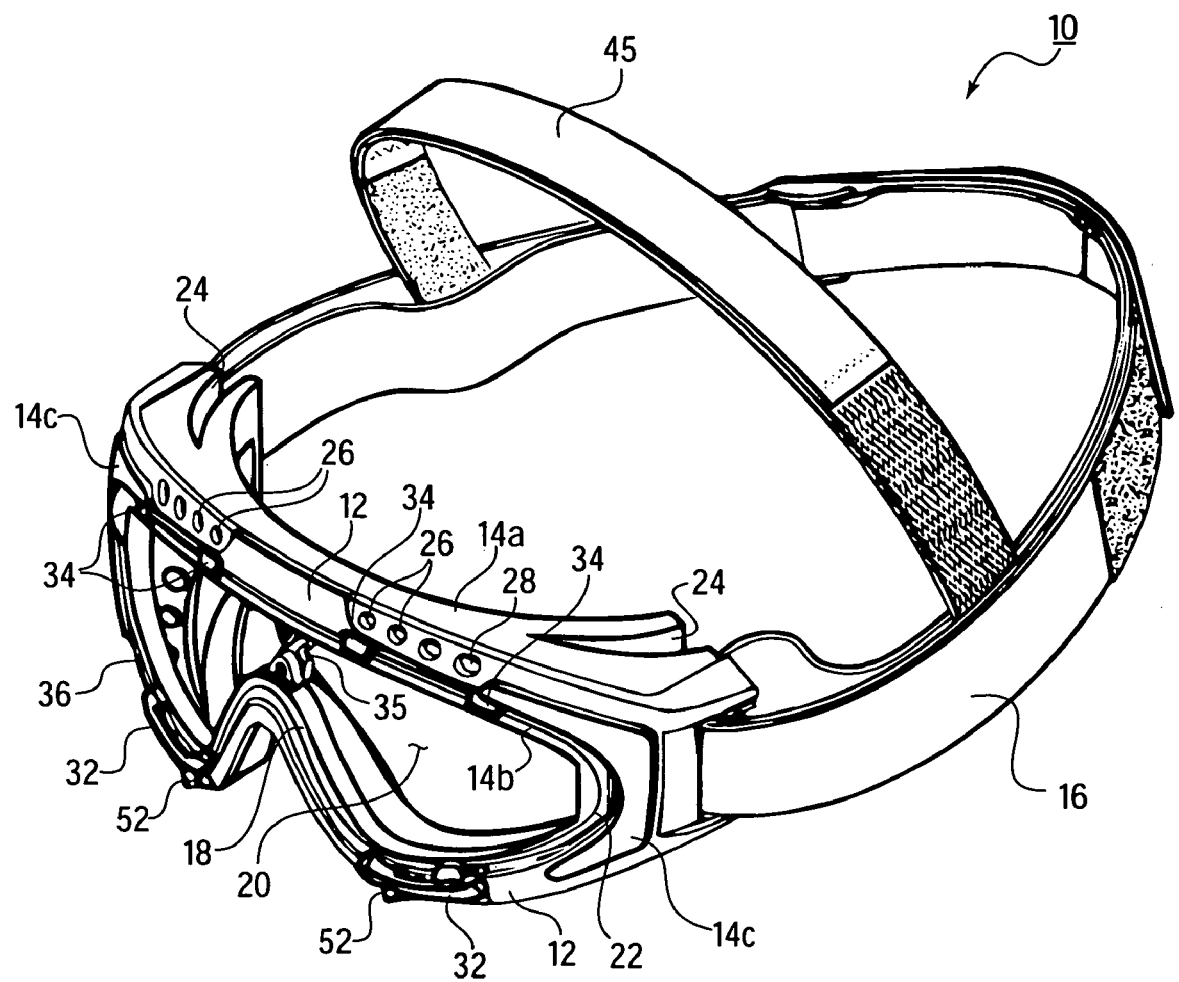
FIG. 1 is a perspective view of an eye protection system in accordance with one goggles embodiment of the present invention.

Referring now in specific detail to the drawings in which like reference numerals identify similar or identical elements throughout the several views, and initially to FIG. 1, an isometric view of one embodiment of an eye protection system 10 in accordance with the present invention is shown. System 10 includes a resilient frame 12 preferably formed using a polymeric material, such as, a resilient plastic, for example, polycarbonate, polyamide, etc. Frame 12 supports an elastomeric sub-frame 14. Sub-frame 14 provides many advantageous features to system 10. These features include, inter alia, providing a seal against the face of a user (in region 14a), providing a comfortable interface for the user (in region 14a), providing a seal for a lens (in region 14b) and permitting facial movement (anthropometric adjustments) without lens movement relative to the eyes of the user (in regions 14c).

Frame 12 preferably receives portions of sub-frame 14 at or near attachment points for an adjustable strap 16. In this way, flexibility is provided in system 10 wherein the frame 12 and sub-frame 14 are permitted to flex with minimal impact displacement of the periphery of a lens 20 relative to frame 12 and sub-frame 14. Sub-frame 14 includes a portion 18, which extends over a portion (not shown) of frame 12. A lip 22 extends from portion 18 to provide a gasket against which lens 20 forms a seal when installed. Sub-frame 14 includes corrugations 24, which provide additional deflection capability of sub-frame 14 while maintaining frame 12 and lens 20 in place. Frame 12 includes vent holes 26 to permit fresh air to enter and to permit humidity to escape from a space created between a user and lens 20 when system 10 is worn. Sub-frame 14 includes vent holes 28 in communication with holes 26 to provide an air path between the space between the user and lens 20 and the ambient environment. Vent holes 26 and 28 may be placed at other locations on system in addition to or instead of the locations shown. A filter or screen may be provided over holes 28 or holes 26 to prevent particles, dust, etc. from entering the space between the user and lens 20. In one embodiment, a screen (not shown) is adhesively bonded to the elastomeric material of sub-frame 14. In other embodiments, the screens are attached to sub-frame 14 via placement of the screens onto a polymer frame and then attaching this frame to sub-frame 14.

System 10 includes release mechanisms 32 preferably located at a lower portion of system 10. Release mechanism 32 works in conjunction with tabs 34 which are formed in frame 12 on an opposing side of lens recess 36 relative to mechanisms 32. An adjustable head/helmet strap 45 may also be included. Strap 16 may include additional features to adjust the circumference of strap 16, which are needed for accommodating different head sizes, helmet sizes, and helmet shapes. This strap 16 can be worn over or under different helmet systems depending upon the need. Another function of vertical strap 45 includes keeping the strap in place when placing it on the helmet and then may be moved toward the face of a user to secure strap 16 in position.

A support 35 is included to provide additional support to frame 12. In addition, support 35 contributes to the structural integrity of system 10. Support 35 may be attached to portions of frame by employing fasteners such as screws or rivets, for example.

Figure 2B:
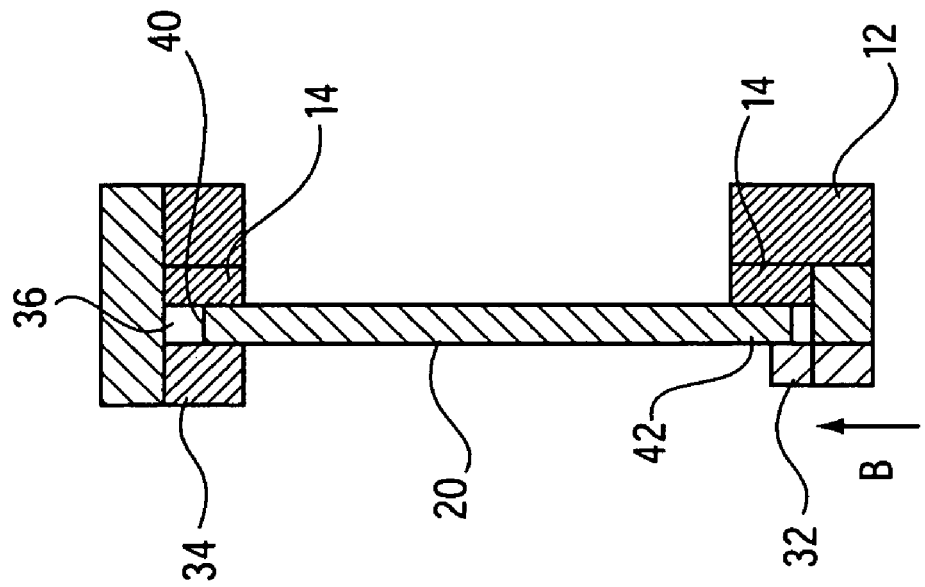
FIGS. 2A and 2B are schematic cross-sectional views showing the installation of a lens in accordance with one embodiment of the present invention.
Figure 2A:
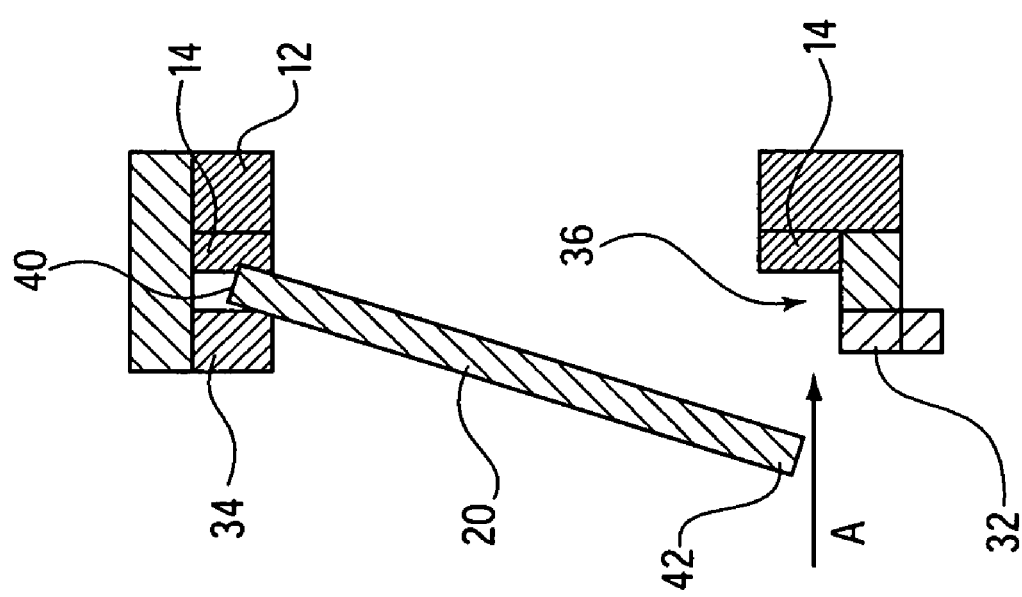

Referring to FIGS. 2A and 2B, installation of a lens 20 is schematically shown in a cross-sectional view in accordance with an illustrative embodiment of the present invention. Lens 20 (illustratively shown as straight instead of curved) is mounted within recess 36 by introducing a top edge 40 of lens 20 at an angle into recess 36. Top edge 40 is held in the front by tabs 34 and in the back by sub-frame 14. While release mechanism 32 is retracted, a bottom portion 42 of lens 20 is inserted into recess 36 in the direction of arrow "A". Release mechanism 32 is advanced in the direction of arrow "B" to hold lens 20 in place and apply a preload against lens 20 to form a seal against sub-frame 14 which lines recess 36. Tabs 34 and release mechanisms 32 are advantageously located at the periphery of lens 20. In this way, field of view obstruction is minimized.

Figure 3B:
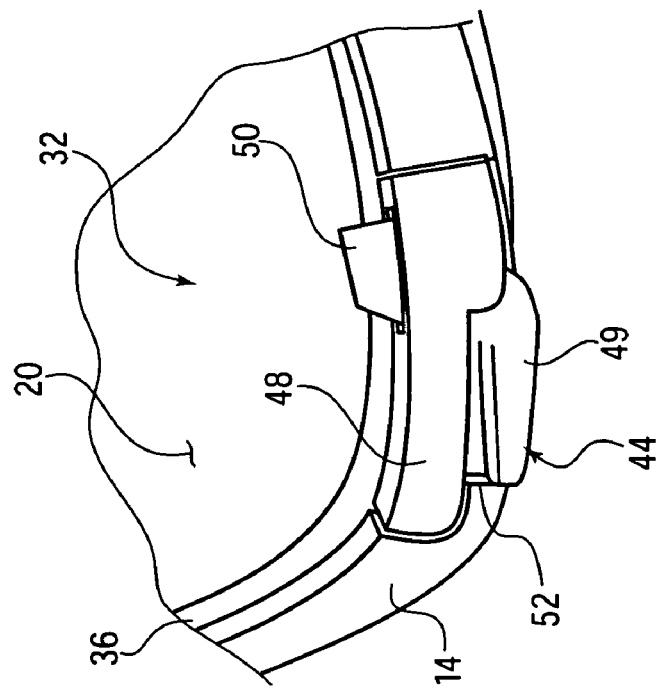
FIGS. 3A and 3B are elevation views of a release mechanism in open and closed states, respectively, in accordance with one embodiment of the present invention.
Figure 3A:
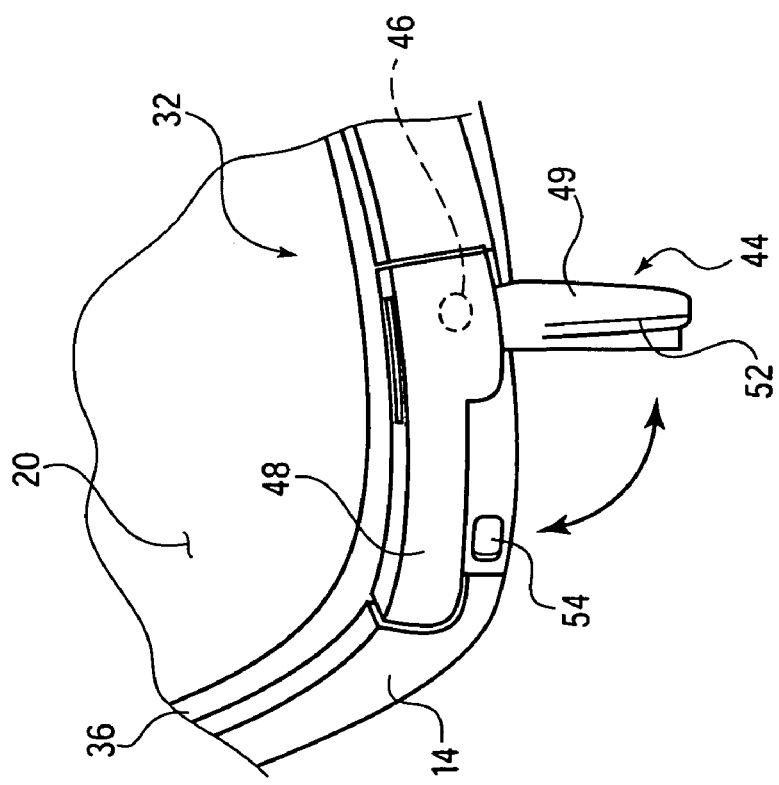

Referring to FIGS. 3A and 3B, release mechanism 32 includes a plurality of useful features. Release mechanism 32 includes a lever arm 44, which is pivotally attached to frame 14. A peg 46 (shown in phantom lines) is preferably integrally formed in frame 14. Lever arm 44 includes a hole formed therein, which receives peg 46. A cover portion 48 fits over lever arm 44 and engages peg 46 to prevent lever arm 44 from being dislodged from peg 46. Lever arm 44 includes an integrally formed handle 49 on a first end portion and an engagement portion 50 on a second end portion. When lever arm 44 is rotated to a first position, engagement portion 50 is retracted into cover portion 48 clearing the lower periphery of lens 20 as shown in FIG. 2A, permitting lens 20 to pivot forward out of recess 36 at that location. When lever arm 44 is rotated to a second position, engagement portion 50 is advanced past cover portion 48 over a portion of lens 20 permitting lens 20 to be retained and preloaded in recess 36 at that location. When lever arm 44 is in its second position (to maintain lens 20 in recess 36), a protrusion (not shown) formed on lever arm 44 engages a hole 54 formed in frame 12. In this way, lever arm 44 is secured to prevent lever arm 44 from rotating and thereby releasing lens 20 from its secured position. A handle 52 is provided so that a user can move lever arm 44 between positions without the use of tools and can remove the lens 20 from the goggle/spectacle while wearing gloves. Advantageously, the lens 20 can be changed without doffing and then donning the goggle.

Recess 36 and sub-frame 14 of system 10 provide sufficient tolerance to support a wide range of lens thicknesses. In one embodiment, the elastomeric material of sub-frame 14 in recess 36 includes a spring constant (elastic or Young's modulus) sufficient to accommodate a range of thicknesses, for example, of between about 0.5 mm and about 6 mm. Lever arm 44 of release mechanism 32 provides sufficient rigidity to support the compressive forces resulting from the deflection of sub-frame 14. This feature of the present invention substantially improves the capabilities and interchangeability of lens within system 10.

The method for securing and releasing lens 20 provided in system 10 permits easy installation and removal of lens 20 without the use of tools. This permits easy replacement of lens 20 to adapt system 10 for a new threat or to simply replace the lens 20 with a new lens. It is to be understood that other types and kinds of release mechanisms may be employed in accordance with the present invention. These may include, among other things, biased lever arms, snaps, fasteners or other securing devices located at the periphery of the lens to ensure the lens is retained properly in its platform.

Figure 4B:
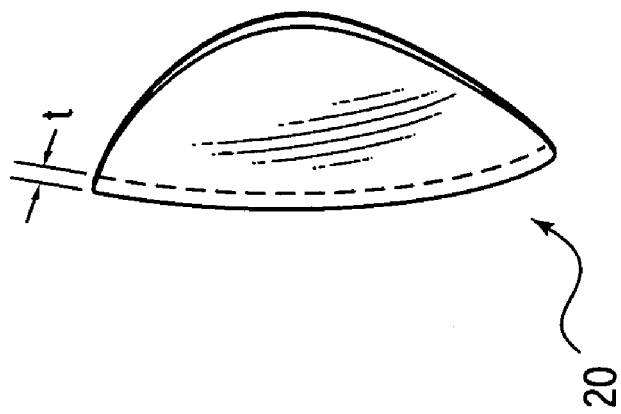
FIGS. 4A and 4B are a front and side view, respectively, of a multiple threat lens for the eye protection systems of the present invention.
Figure 4A:
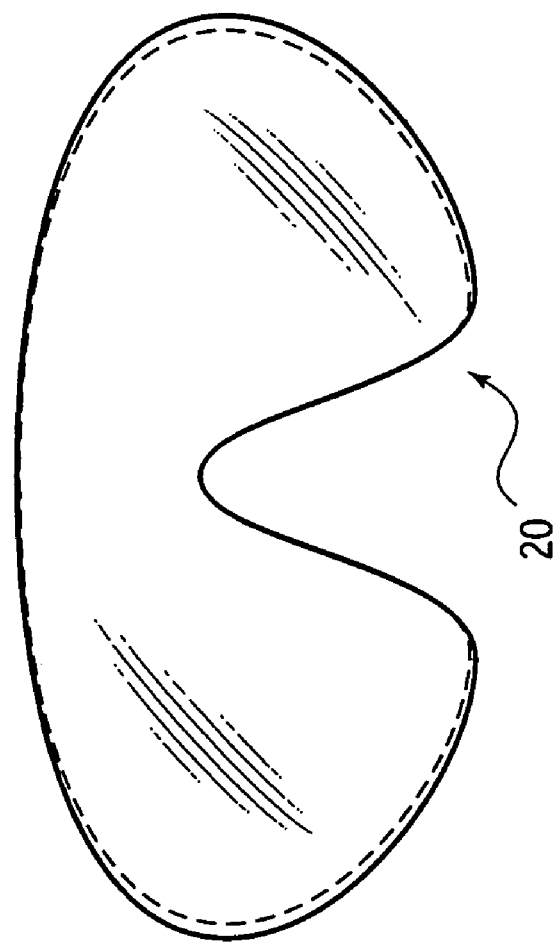
Figure 5:
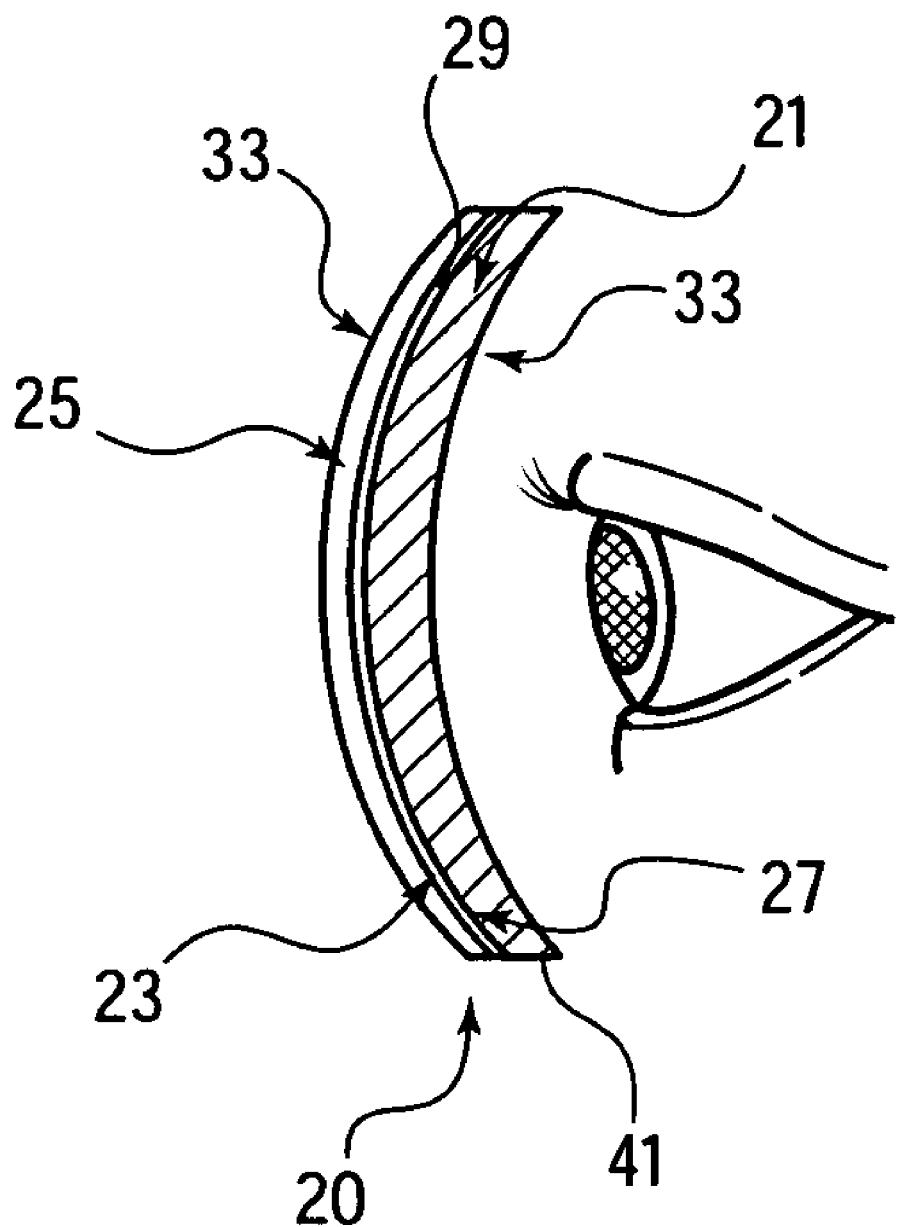
FIG. 5 is a schematic cross-sectional view of a laminate lens assembly in accordance with the present invention.

Referring to FIGS. 4A, 4B and 5, lens 20, in accordance with the present invention, provides ballistic protection for a user. As such, lens 20 includes a transparent or semi-transparent resilient material. In a preferred embodiment, a polycarbonate material is employed for lens 20. Lens 20 preferably includes a thickness "t" of between about 0.5 mm to about 6 mm. Lens 20 includes a plurality of different types, each type for addressing a different threat or plurality of threats. For example, one lens type may include a clear polycarbonate designed for ballistic protection while another may include additional dyes or additional layers for light protection.

Dyes may be introduced into or on the polycarbonate material for ultra violet radiation protection, sun light protection, visible light protection, infrared protection, etc. Dielectric stacks may be included in lens 20 to provide protection from predetermined wavelengths or spectrums of light. In addition, holograms or other optical features may be included. Different combinations of all of the above-mentioned features are also contemplated for lens 20.

Lens 20 includes a compound curvature adapted to provide a zero power plano lens with minimal distortion. The lens 20 may also be provided with a spherical curvature on both inner and outer surfaces. Lens 20 may also include toric and/or aspherical curvatures.

Figure 4C:
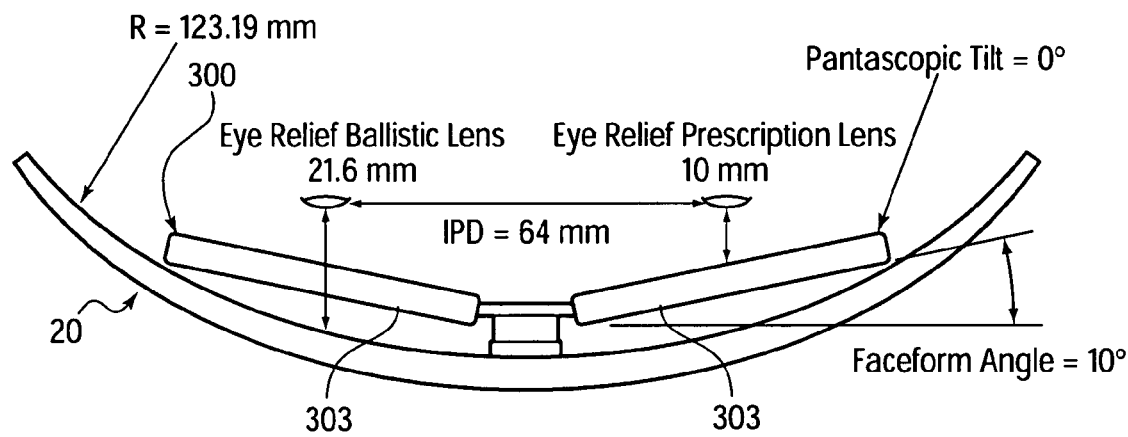
FIG. 4C is a cross-sectional view through the lens of FIG. 4A and a prescription lens carrier in accordance with one illustrative embodiment of the present invention.

Referring to FIG. 4C, the selection of the proper lens curvature was one important aspect of the present invention. To address limitations dictated by field of view requirements and the desire to maintain lens compatibility between the goggle and spectacle, the present invention provides a useful lens design, which is interchangeable between platforms and protects against multiple threats without interfering with the field of view of the user. Goggles tend to have flatter lens curvatures, meaning their radius of curvature is greater. This is due to the way a goggle fits on the face. The goggles normally contact on top of the brow and around the cheekbones to fit the anthropometric features of a human. Therefore, a flatter lens is needed for goggles. Sunglasses move to a smaller radius to achieve the wrap around effect found in popular sports sunglass designs. Sunglasses or spectacles need to employ as low of a radius of curvature as possible, while continuing to provide necessary form, fit and function. The unlikely combination of these features was advantageously achieved in accordance with the present invention. In accordance with one aspect of the present invention, the same lens employed for a spectacle can now be employed in goggles without reducing the effectiveness of the goggles.

For the best performance of the present invention, faceform angle and field of view parameters were carefully addressed and selected. These parameters (i.e., faceform angle and field of view) were considered for each system alone and each system when worn with a prescription lens carrier 300 (results in reduced field of view). Field of view requirements for the lens systems of the present invention included measurements at each of the major meridians around the lens: superior, inferior, temporal and nasal directions (measured at 45 degree increments). The field of view is a result of the trim size of the lens, the amount of eye relief (for the pupil to the inner surface of the plastic lens), and the lens curvature. Other requirements on the prescription lens carrier 300 included faceform angle, measured from the center of the lens to the point at which the lens carrier hits the inner surface of the plastic lens. FIG. 4C shows dimensions of one preferred embodiment and is provided for illustrative purposes. Other dimensions may also be employed in accordance with the present invention.

Lens 20 preferably does not exceed 20 degrees total, 10 degrees per side for the faceform angle. One reason that face form angle becomes important is that when high corrections are placed into the prescription lens carrier, additional power would be produced in prescription lenses 303 due to the face form angle. In other words, the prescription lenses, which contact the surface of lens 20, are angled relative to the face of the user. This effect could be corrected for by cutting a different lens correction properly altered for the angle. This would result in proper performance of the device. Alternately, a lens curvature may be designed to account for the faceform angle requirements. In one embodiment, a lens curvature of 123.19 mm is included, which permits for a faceform angle of 10 degrees at the designed eye relief of 21.6 mm, while still meeting the optical and field of view requirements of the specification and commercial specifications of ANSI. Z87.1. FIG. 4C shows parameters of one embodiment of lens 20. Other lens curvatures may be employed preferably in the range of +/−5 mm of 123 mm. An illustrative inter-pupilary distance (IPD) is illustratively shown as 64 mm. Pantascopic tilt (tilt angle relative to the face of the user) is illustratively depicted as zero in FIG. 4C.

Goggles tend to have pantascopic tilts of close to zero; however spectacle lenses tend to have much higher pantascopic tilts. Popular sports sunglasses have pantascopic tilts up to 15 degrees. Most of the difference between these two devices is related to how they fit on the head, making it more desirable to have higher pantascopic tilts with spectacles than goggles. This creates problems when trying to have a common lens between both a goggle and a spectacle because of optical and laser eye protection concerns. Varying the pantascopic tilts more than a few degrees either positive or negative will cause problems in meeting critical optical and ANSI Z87.1 parameters such as prism and power. Certain technologies used in laser eye protection are limited in the amount of pantoscopic tilt that can be accommodated while still retaining similar amounts of protection.

One embodiment of the present invention includes pantoscopic tilt of lens 20 at a nominal tilt of 3 degrees. The "as worn" design of the goggle is set at 0 degrees, while the spectacle is set at 6 degrees for this illustrative embodiment. Advantageously, this design permits for a single lens design to be utilized between goggle and spectacle, while still meeting the optical and laser eye protection requirements.

Table 1 illustratively shows fields of view (FOV) with and without the prescription lens carrier (PLC) at a plurality of eye locations (45 degree intervals).

TABLE 1

FOV requirements

| Location (45 increments) | Without PLC (in degrees) | With PLC (in degrees) |
|---|---|---|
| Nasal | 27 | 27 |
| Superior Nasal | 32 | 32 |
| Superior | 32 | 32 |
| Superior Temporal | 54 | 38 |
| Temporal | 86 | 55 |
| Inferior Temporal | 67 | 59 |
| Inferior | 37 | 37 |
| Inferior Nasal | 31 | 31 |

The most difficult FOV requirements to meet are with the temporal and superior temporal regions. Users tend to wear either the goggle or spectacle closer to their eyes than the design eye location. This results in an increased amount of FOV.

Advantageously, lens 20 includes a unitary design. No holes or slots are formed within the lens 20. In this way, stress risers and discontinuities, which can potentially compromise ballistic performance, are eliminated.

In preferred embodiments, lens 20 may include a composite of material layers to protect against different threats (e.g., wavelengths of light) and/or provide structural characteristics to lens 20 (e.g., strength/ballistic resistance). In one embodiment, a single base ballistic lens 21 that passes ballistic requirements as a single stand-alone device is included.

Lens 21 also serves as the foundation for attaching other technologies. For example, dielectric (DE) stacks 23 may be formed on a cap lens 25 as inorganic metal oxides. For example, dielectrics such as, titanium oxide, silicon oxide, etc. may be employed. Cap lens 25 includes DE stack 23 formed thereon. DE stacks 23 include a plurality of layers having different refractive indexes and being of thicknesses designed to cause interference of particular wavelengths of light. DE stack 23 may be damaged in tension or during flexing. This is a particular concern when attaching DE stacks 23 to highly flexible polymers such as polycarbonate. By attaching cap lens 25 to ballistic lens 21 a higher level of support is achieved thereby reducing the concerns for damaging DE stack 23 when formed on polymer materials such as polycarbonate. Lens 21 and cap 25 are preferably made out of polycarbonate materials. Lens 25 may also be made out of glass, with ballistic protection being provided by inner lens 21. Lens 21 may also include a hologram 27 or other layer to provide laser light protection, such as an organic dielectric stack or non-linear optical device. Hologram 27 may be stretched onto lens 21 by known processes. Lens 20 may include one or both of DE stacks 23 and holograms 27. Lens 20 may simply include lens 21 or any combination of items described herein.

The addition of cap 25 should not interfere with the attachment mechanisms for the goggles (system 10) and spectacle (systems 100 and 200 described below) lenses. Both the goggle and spectacle use different means for attaching the lenses; therefore, these attachment areas should not interfere with the line of sight of the user. Cap 25 may include an optional anti-reflection coating (ARC) 33. ARC 33 may be provided on any lens surface described herein.

Figure 6A:
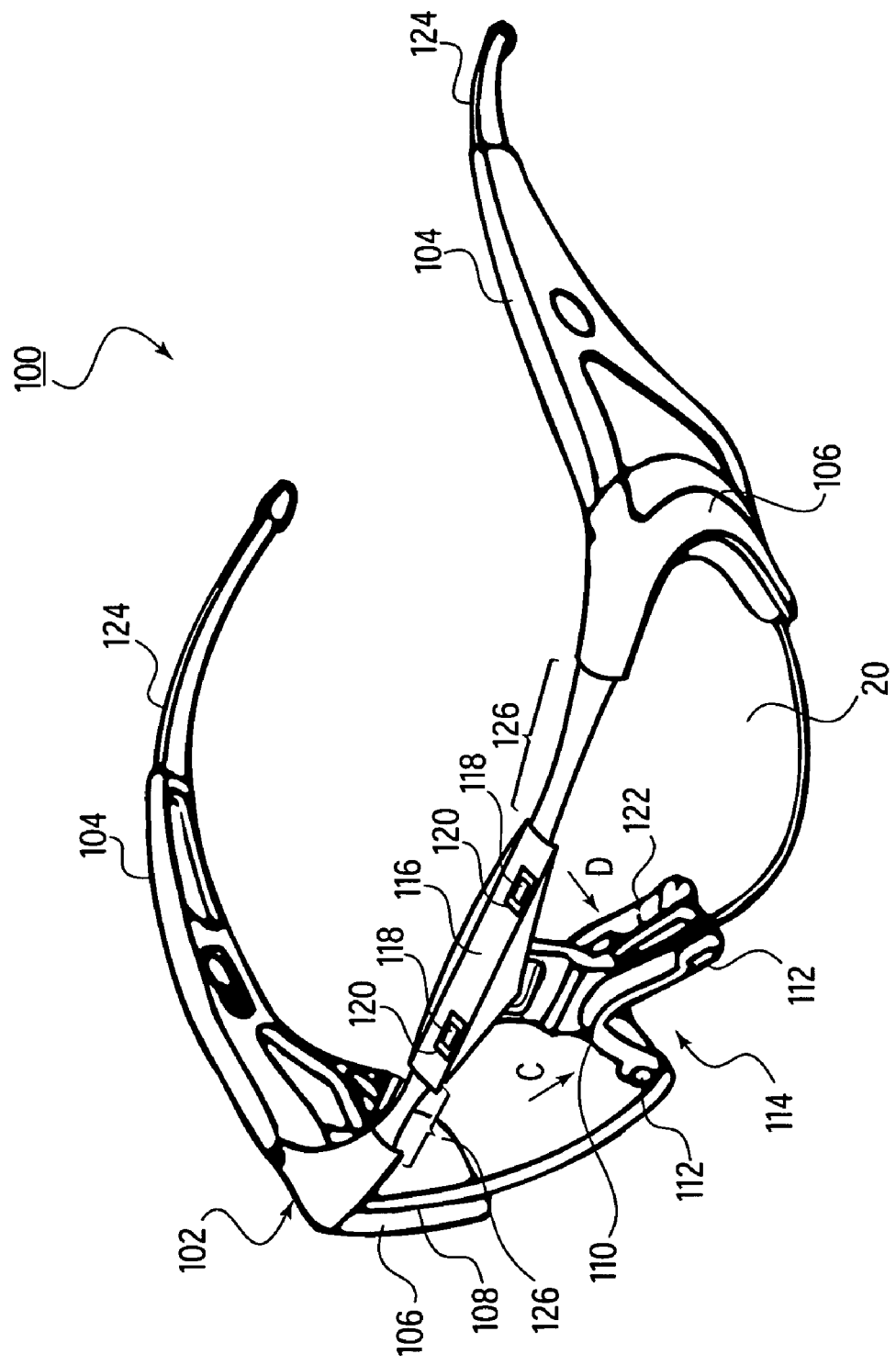
FIG. 6A is a perspective view of an eye protection system in accordance with another spectacles embodiment of the present invention.

Referring to FIG. 6A, since lens 20 is secured at its periphery. Lens 20 is interchangeable on a plurality of platforms. One such platform includes, for example, a spectacle system 100. Spectacle system 100 includes a frame 102. Arms 104 are pivotally connected to frame 102. Frame 102 includes extensions 106, which are configured and dimensioned to receive lens 20 therebetween. Extensions 106 form a groove 108 on an internal edge such that when lens 20 is installed, lens 20 is captured in groove 108. A support 110 is included which is mountable on frame 102. Support 110 attaches to frame 102 in a way that permits some deflection of support 110.

Figure 6C:
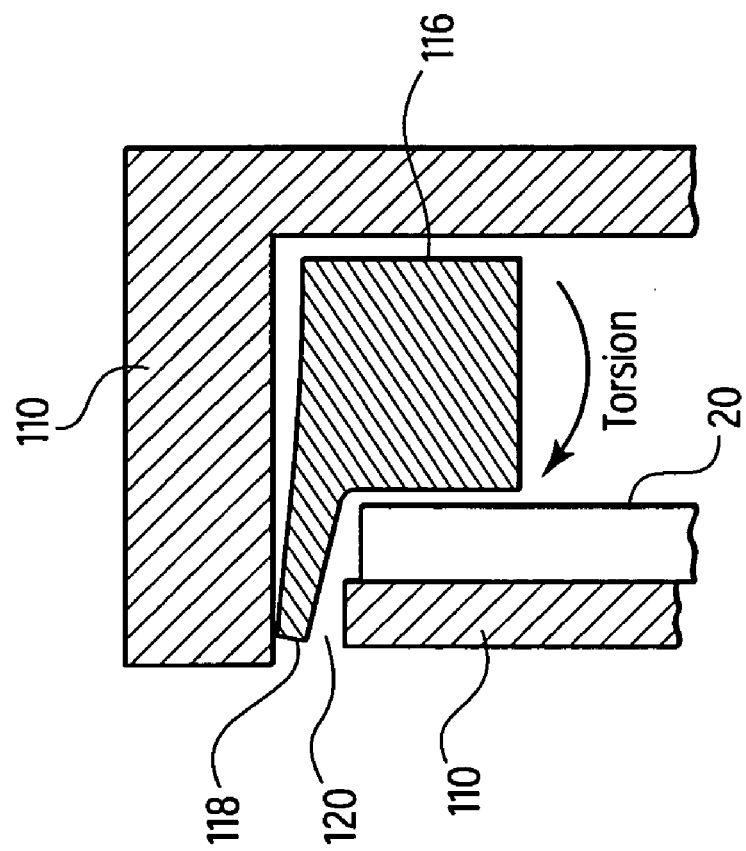
FIGS. 6B and 6C are magnified schematic cross-sectional views showing the installation of a lens in the spectacles of FIG. 6A which provides a torsional preload in accordance with one embodiment of the present invention.
Figure 6B:
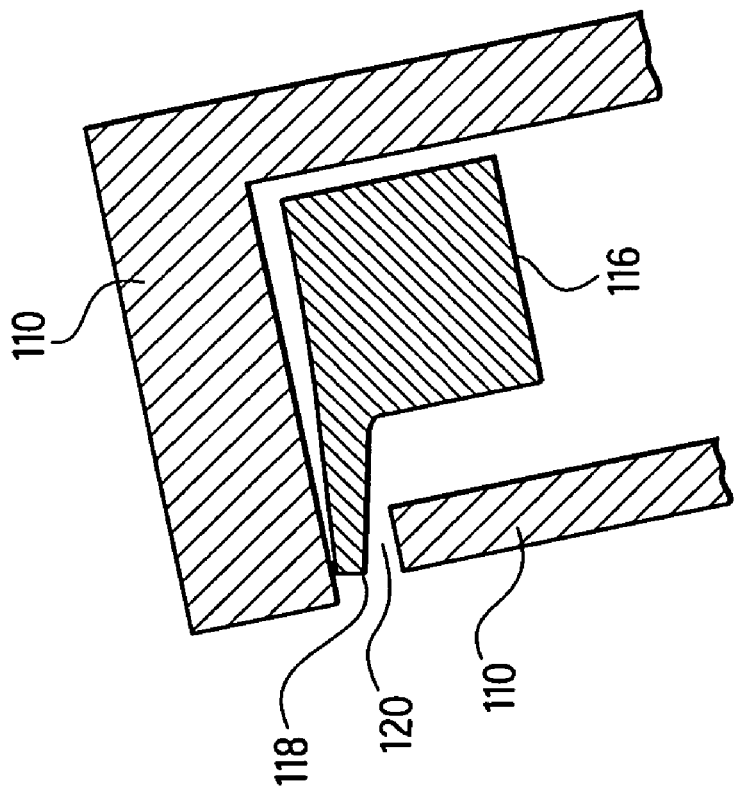

Referring to FIGS. 6B and 6C with continued reference to FIG. 6A, support 110 is capable of deflecting forward to accept lens 20. Once lens 20 is installed, clips 112 on nosepiece 114 are secured against lens 20 and clips 112 are preloaded against lens 20 to secure lens in spectacle frame 102 as a result of the deflection of support 110. Frame 102 includes a brow bar 116, which is designed to provide the preload to secure lens 20 with clips 112. Brow bar 116 is a flexible member capable of providing sufficient strength and flexibility to support ballistics requirements for system 100. For example, the spectacles of the present invention were subjected to a ballistic test in accordance with MIL-STD-662E using a 0.15 caliber, 5.8 grain, T37 shaped projectile fired at 640–660 feet per second (fps). The goggle and spectacle were both tested up to at least 700 fps and lens 20 was tested at speeds as high as 850 fps. The test required that at no time can the projectile come through the device (e.g., lens 20) and break a witness plate mounted on the inside of either the goggle or spectacle. In addition, no components coming off of either device could penetrate this witness plate as well. The designs described herein were designed to pass at least this ballistics test.

In one embodiment, torsion is developed in support 110 by providing tabs 118 integrally formed in brow bar 116. Tabs 118 are inclined relative to the orientation of support 110 to provide an angular displacement of support 110 in an unloaded state (e.g., no lens in FIG. 6B). Tabs 118 are formed to engage holes 120 such that upon introducing lens 20 into spectacle 100 (FIG. 6C) and securing lens 20 with clips 112, support 110 develops torsion in brow bar 116. This torsion is employed to secure lens 20 in place. Tabs 118 are formed such that an angle is naturally formed which represents a torsional deflection when support is rotated to accept lens 20.

Clips 112 of nosepiece 114 may be installed by depressing clips 112 toward each other (in the direction of arrows "C" and "D") to get past a nose arch portion of lens 20. Clips 112 are then released outward to engage and retain lens 20 within spectacle 100. Nosepiece 114 may include a soft or elastomeric pad 122 to provide comfort for a user. Arms 104 may also include pads 124 to provide comfort for a user.

During ballistics testing, performed by the inventors, upon impact, spectacle system 100 oscillates. Such oscillations need to be damped to prevent collateral damage to a user. To increase the damping capabilities of spectacle system 100, the present invention employs flexible zones 126 between contact points (support 110 and arm 104). These flexible zones 126 contribute significantly to the damping of oscillations through spectacle system 100. Frame 102 of spectacle system 100 is formed using flexible materials, such as, for example, polycarbonate, polyamide (nylon) or polyester. Blends of these and other materials are also contemplated. Flexible zones 126 may be provided in brow bar 116 by forming slots therein or reducing the cross-sectional area of brow bar 116. Advantageously, the oscillatory response of spectacle system 100 can be determined and brow bar 116 may be designed such that damping effects are maximized.

A relationship between the geometry of brow bar 116 and the oscillatory response has been determined using high-speed photography. When lens 20 is hit with a projectile a very violent oscillatory response ensues. Surprisingly, a reduction in the rigidity of frame 102 improves the oscillatory response to a ballistic projectile despite the rigidity provided to the structure by lens 20. If lens is held too tightly the material may be caused to break. By holding the lens less tightly, the lens is able to oscillate easier resulting in less energy being transmitted directly to the frame. Materials utilized for the frame included, for example, nylon and polycarbonate. Nylon, while a flexible material, is not as good a material in impact as polycarbonate, which has more ductile material properties permitting the polycarbonate lens frame to more efficiently absorb impact forces. A reduction of the cross-sectional area in zones 126 of say, about 5% to about 80% may be employed depending on the ballistic protection needed. This reduction is measured from the end portions of regions 126 to the center portion of regions 126. The change in cross-sectional area is preferably gradually transitioned to reduce stress. It is preferable that regions 126 include well-radiused and blended tapers to reduce stress-risers in these regions.

Figure 7:
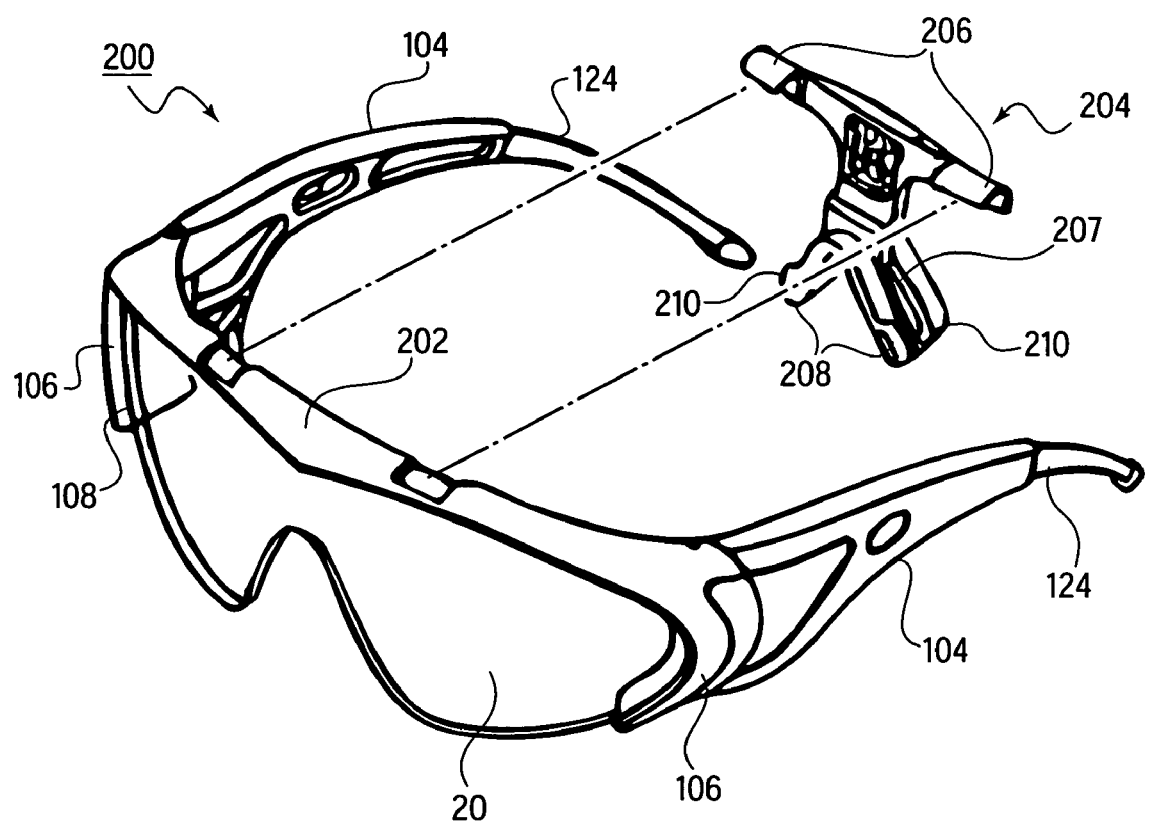
FIG. 7 is a perspective view of another spectacles eye protection system with a support removed to show how a lens is secured to the frame of the spectacles in accordance with yet another embodiment of the present invention.

Referring to FIG. 7, an alternate embodiment of a spectacle system includes spectacle system 200. Spectacle system 200 includes a brow bar 202, which is more rigid than brow bar 116 of system 100. A support 204 includes clips 206 for brow bar 202 engagement and clips 208 for lens 20 engagement. Support 204 includes a nosepiece 207 having opposing end portions 210 which can be compressed inwardly toward each other to permit lens 20 to pass over nosepiece 207 during installation. Upon release of compressed end portions 210, clips 208 secure lens 20 while simultaneously clipping lens 20 to brow bar 202 with clips 206 to secure lens 20 in system 200.

Figure 8A:
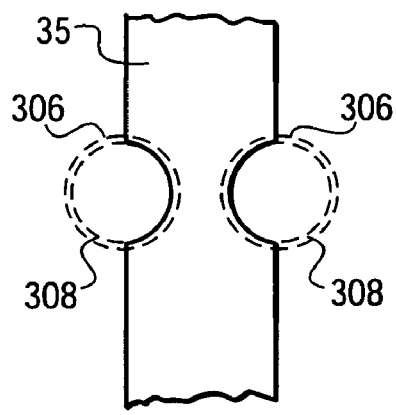
FIGS. 8A and 8B are schematic views showing attachment schemes for the prescription lens carrier of FIG. 9 for the eye protection systems of the present invention.
Figure 8B:
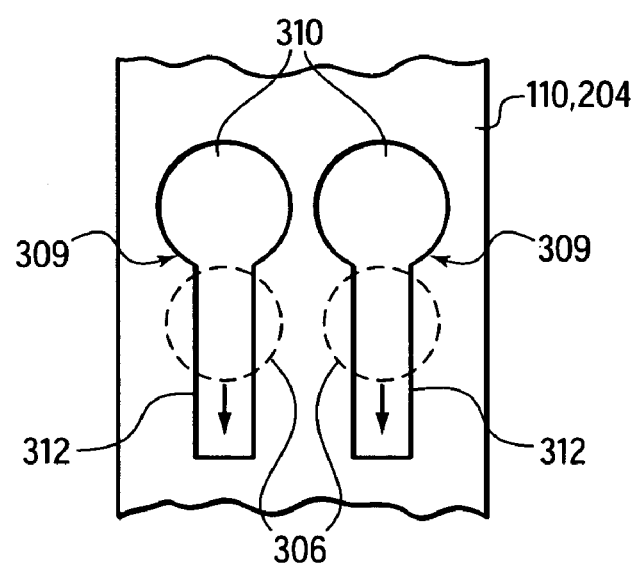
Figure 9:
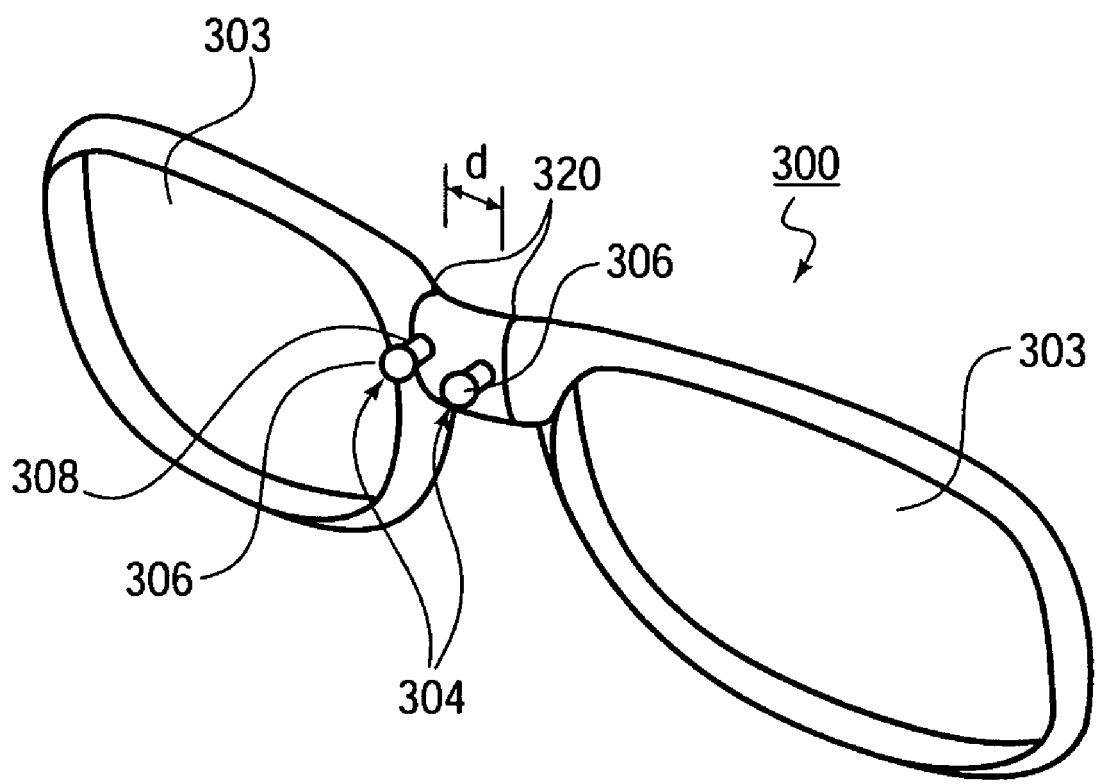
FIG. 9 is a perspective view of a prescription lens carrier in accordance with another embodiment of the present invention.

Referring to FIGS. 8, 9A and 9B, support 35, support 110 and/or 204 may be adapted to receive a prescription lens carrier 300. Lens carrier 300 preferably includes snap-in features 304 for detachably fastening lens carrier 300 to support 35, 110 or 204. Advantageously, lens carrier 300 is attached to system 10 (or system 100 or system 200) at or over the nose of a user. In this way, a stable attachment point is provided so that facial or body movements do not impact the position of lens carrier 300. This is particularly useful for system 10 where goggles are strapped to the head or to a helmet of a user and facial movements effects the movement of goggles. By having an attachment point near the nose of the user, physical movements of the user have less impact on the alignment of lens carrier 300 with the eyes of the user.

Lens carrier 300 is adapted to receive prescription lenses 303 for individual users. Lens carrier 300 preferably includes two protrusions 304 or other mechanical features. Protrusions 304 are separated by a lateral distance d to provide stability for lens carrier 300 relative to the platform on which lens carrier 300 is mounted.

In one embodiment for system 10, for example, protrusions 304 each include a bulbous portion 306. Protrusions 304 are compliant to permit them to flex. In this way, protrusions 304 separate by a camming motion of portions 306 against grooves, which accept portions 308 in support 35 during installation. (Portions 306 are shown in phantom lines in FIG. 8A). Once past the depth of support 35, protrusions 304 unflex back to their original position thereby locking lens carrier 300 in place. Lens carrier 300 may be detached by pulling lens carrier 300 away from support 35 to initiate the same camming motion during the removal of lens carrier 300.

In another embodiment for systems 100 and 200, for example, grooves 309 are provided in support 110 or 204, bulbous portions 306 of protrusions 304 are inserted into holes 310 and then slid along slots 312 to secure lens carrier in place. (Portions 306 are shown in phantom lines in FIG. 8B).

By providing a separate lens carrier, lens 20 does not need to provide vision correction features. In addition, the design of systems 10, 100 and 200 do not need to accommodate typical frames employed with corrective lenses.

Lens carrier 300 may include flex zones 320 in a center portion to permit deflection and flexibility within lens carrier 300. While lens carrier 300 has been shown and described in accordance with a specific embodiment, other attachment and detachment methods and structures are contemplated by the present invention. It is preferable that these structures and methods include multiple laterally offset attachment structures to ensure stability of the lens carrier, and provide an attachment point at a stable portion of the system to which the lens carrier is attached to permit facial and body movements of the user without interfering with the alignment between the prescription lenses and the users eyes.

The present invention provides for interchangeability of lens 20 between lens mounting platforms. Those skilled in the art understand that goggles and spectacles have different design requirements for lenses, which are mounted therein. Goggles typically include a greater stand-off (i.e., distance from the eyes of the user) than a spectacle. Therefore, goggles typically include a more planar shape than spectacles. In addition, spectacles provide more in the way of wrap-around protection. Thus, the spectacles typically form a more rounded or spherical shape. Since these designs include different requirements and shapes, one skilled in the art would not be motivated to use a lens adapted for a goggles design with a spectacles and vice versa.

The present invention provides systems and lens designs which provide for interchangeability between goggles and spectacles while providing for ballistic protection and low distortion of light through the lens for both platforms. The completed lens assembly of the present invention fits into both a goggle and a spectacle. Lenses of any type, for example, clear, sunshade, laser protection, or other lenses fit in both platforms and are interchangeable therebetween. This was particularly challenging since the goggles and spectacles are preferably employed for military applications. The goggles (e.g. system 10) preferably are a one size-fits-all design. Field of view, lens tilt, and eye tolerances needed to be considered and maintained for proper eye alignment in the various platforms.

A sandwich or composite lens approach with multiple technologies present is provided in accordance with the present invention. The lens configuration includes many advantages over prior art solutions. Holograms and DE stacks afford limited scratch resistance, and if scratched, the laser protection would be completely lost in that area, rendering the item useless. It may take approximately a pico-second exposure of a particular laser at a given strength to completely damage the retina of a human eye. The holograms in particular are vulnerable to exposure to water vapor and weather. The holograms and dielectric stacks degrade when exposed to some of the common battlefield chemicals and other materials (e.g., insect repellants, hydraulic fluids, different types of fuels, and high concentration chlorine). The sandwich construction as shown in FIG. 5 for lens 20 includes two separate lenses with holograms and dielectric stacks protected inside. The completed assembly fits in both a goggle and spectacle as described above for all lens types (e.g., clear, sunshade, laser).

Referring again to FIG. 5, lens 20 includes cap lens 25 and base lens 21 which be treated with dyes on surfaces thereof or have dyes introduced into the solid matrix or substrate of lenses 21 and/or 25. A dye (chromophore, absorber, colorant) may include a substance, which adds color to substrates to which the dye is added (e.g., plastic, or glass for lens 20). The dye may be introduced to absorb light in the visible region or other region of the electromagnetic radiation spectrum and thereby transmit and/or reflect colored light through/from the substrate in which the dye resides. More broadly, a dye is any substance, which absorbs light in a region of the spectrum of interest to the observer. Thus, a specific dye may be introduced to absorb light in a specific band or bands in the electromagnetic spectrum (e.g., UV, VIS, NIR, IR, microwave, etc.) in accordance with the present invention.

In preferred embodiments, a dye or other compound may be introduced into lens 20 to absorb light in the visible, near infrared and/or ultraviolet regions of the spectrum. The presence of the dye in the substrate may or may not have coloration detectable to the human eye. Dyes employed in the present invention may include organic compounds which are soluble in polymers and which modulate the light passing therethrough. Such dyes may include dyes from the families of metallo-porphyrins, metallo-phthalocyanines, aza-variants of these, annellated variants of these, squaryliums, croconiums, aminiums, diimoniums, cyanines, etc.

Dyes may be selected and added to lens 20 for absorbing or filtering out specific laser wavelength, UV radiation, NIR, IR or any visible light (e.g., sunshade). Dyes may be employed in lens 20 in combination to filter multiple wavelength or bands of wavelengths, which would otherwise be permitted to pass through lens 20.

Dielectric stacks 23 may be included in lens 20 to further reject wavelengths of light through destructive interference. When a wave front of some characteristic wavelength encounters a sequentiation of baffles (each being a molecular/atomic/ionic species in some plane), the wave front can be interfered with in a number of modes but most modes of interest are destructive (waves reflected from the front surface being exactly out of phase with those reflected from the rear surface to give negated waves).

If the front and rear surfaces are separated spatially by an odd integral number of quarter wavelengths of the incoming wave in the direction of the incoming wave, then interference can be expected. When applied to light, and the "baffles" are a sequentiation of materials of chosen thicknesses but which repetitively alternate in being one of high index of refraction and one of low index of refraction, then the interface between any two layers behaves as a mirror. If the thickness of each layer is rigorously an odd integral number of quarter wavelengths of the incoming light, then the light will be interfered with. Since some of the light gets transmitted through the "mirror" (it is not a perfect mirror), multiples of this first alternated layering will be needed to reject light of the given wavelength. Since the light may encounter the stack 23 at many different angles experiencing a different path of flight within that layer with each angle of incidence, then the layer thicknesses have to be appropriately altered in subsequent layers to account for nonorthogonal angular encounters which are to be similarly interfered with.

If there is more that one wavelength which is to be interfered with, then additional layers are added for each wavelength to be considered. The end result is a large number of layers or stack to accommodate off-angle hits up to some maximum angle, various wavelengths of light, and sequential identical layers to account for light leakage from one layering to the next.

To construct dielectric stack 23 using a high refractive index material like $SiO_2$ and a low refractive index material like $TiO_2$ in such a way as to reject all wavelengths of light in the range from say the end of the visible spectrum to from 680 nm to 1100 nm for all angles of incidence within say 50 degrees of normal incidence, then the resulting dielectric stack will be hundreds of layers thick and as a unit will be perhaps between 15 and 20 microns thick.

For reference, optical hard coatings placed on lenses for scratch resistance may be about 3 to 5 microns thick and are composed of an inorganic/organic polymeric mix called a polysiloxane. Adhesion of same to an all organic lens surface like one of polycarbonate often takes use of primers and careful chemical processing to ease the transition of the chemistry of the all organic substrate to the organic/inorganic coating. Thus, with dielectric stack 23 which may be all inorganic to adhere to an all organic polymeric substrate, a similar transitional "primer" or subcoating is used which again is a mix of organic and inorganic chemical moieties to bridge the drastic transition of the differing chemistries. Differences in moisture absorption, thermal coefficient of expansion, etc. often are the reasons why the inorganic stacks may fail in delaminating from the organic substrate under environmental stresses of temperature changes, moisture, etc.

Although in theory such dielectric stacks can be deposited (most are done best via high vacuum sputtering processes) so as to interfere light of any wavelength, most success has been seen in achieving this in the red and near infrared portions of the spectrum and in doing so minimally affecting the visible region of the spectrum by not detracting from desired transmission of useful wavelengths of light.

Dielectric stack 23 may include a rugate. If in a sputtering process, where species of high and low indices of refraction are being deposited on a substrate sequentially in a dielectric stack, both species of high and low indices of refraction were deposited simultaneously but varying sinusoidally with respect to each other's relative concentration, then a rugate structure is formed. A rugate is a single thickness of mixed species (usually metal oxides) of high and low index of refraction whereby the concentration of one oxide in the other oxide varies sinusoidally in a very controlled fashion as a function of the depth into the coating. If the sinusoidal variation were to be a true step wave (tooth comb), then the rugate would be a layered dielectric stack. Rugates work in destructively interfering with light on the same principles as described above where the periodicity of the concentration variation delivers the wavelength/angle rejection needed. While the rugates can be constructed anywhere in the spectrum, most success to date have been at the blue end (low wavelength) of the visible spectrum.

Dielectric stack 23 may also include an organic dielectric stack. Organic dielectric stacks are analogous to inorganic dielectric stacks, but employ polymers of widely differing indices of refraction to replace the metallic oxides of inorganic dielectric stacks. The polymer films include many layers, which can be laminated onto substrates by various means. Polymethylmethacrylate may be employed, for example, as the high index material and polyethylenenaphthenate the low index material in an organic stack replacing, for example, the $SiO_2$ and $TiO_2$, respectively, of an inorganic stack.

Lens 20 may include one or more glass components (e.g., lenses). Glass is an inorganic polymer, which may include inorganic dyes to modify the spectrum of encountering and transmitted light much as organic polymers may include organic dye molecules. Dyes for inorganic polymers may include metallic ions (e.g., $Fe^{+3}$, $Cu^{+2}$, $Nd^{+3}$, etc.) along with their anionic gegenions (oxide ($O^{-2}$) being the most common). These dyes absorb light totally analogously to organic dyes but differ in two respects: (1) most metallic-ion dyes absorb rather broadly over spectral ranges as opposed to some organic dyes being narrow notch absorbers; (2) the metallic-ion dye absorptions extend farther out into the near infrared region with less impact on the visible region than organic counterparts.

Lens 20 may include dyes, which produce a non-linear optical system. Nonlinear optical systems are different from linear optical systems. For example, in a linear optical system, an absorbing species (dye) absorbs incident electromagnetic radiation which is coincident with an energy excitation from its ground state to its lowest excited state; that absorbed energy is then re-emitted quickly as light or via vibrational cascades as heat or both.

Excitations and relaxations between electronic states of like spin symmetry are the only ones which are not forbidden (i.e., which have nonzero probability of occurring). Transitions from singlet states will be to other singlet states and from triplet states to other triplet states. Spin state crossing is of such low probability that those transitions cause little more than low level noise in a spectrum. In a nonlinear optical system, an absorbing species absorbs incident electromagnetic radiation into an electronic spin aligned excited state. However, the lifetime of the excited state is of such duration that the excited state can cascade into an excited state of unaligned spin. From that excited state, the state can then proceed to absorb radiation to excite to spin aligned states from that excited state which are spin opposed to that of the initial ground state. These excitations, due to absorptions of light by matter in excited states, produce a spectrum, which is totally different from that which would be generated if the intersystem spin crossing had not occurred. It is nonlinear in that part of the initial absorbed energy returns to the ground state and part continues on in a totally separate spectral life line. Dyes that produce the non-linear response may include fullerenes, and derivatives of this family of compounds, for example.

Lens 20 may include a hologram(s) 27. Holograms are photographic images, which can be included internally to a coating or film and can be laminated to a lens. The image is not a classic image, but an image of a spectral region in which light will not be transmitted but reflected—a spectrally select partial mirror. This is effectuated by the film (a dichromated gelatin or a photopolymer) in having its internal local indices of refraction altered by the laser light, which exposed it in generating the desired rejection mirror. The phenomenon is an interference reflection phenomenon. Holograms are most successful in the low wavelength region of the visible region of the spectrum. Holograms are particularly useful in rejecting laser light at predetermined wavelengths in the visible spectrum.

In one embodiment of the present invention, optical requirements for military eye protection systems were met as set forth in the ANSI Z87.1. The present invention is tested for many different requirements such as power, prism, astigmatism, haze, distortion, and visual acuity. Both the unlaminated (clear and sunshade) and the laminated lenses met these requirements.

With continued reference to FIG. 5, one aspect of the present invention is to provide a zero power lens for ballistic protection. To make the laminated (composite) lens 20 plano, the protective cap 25 had to have power induced into it in order to make plano optics out of the assembly because lens 21 is also designed to be a stand-alone lens with plano optics. Cap 25 is shown in FIG. 5 with a portion removed (at the top of the cross-sectional view) to highlight the laminate structure. Power is induced into the lens by carefully selecting the lens curvatures to induce the proper amount of power into the lens assembly. Because the two lenses were being laminated together, the interface of these two lens surfaces is one important aspect of the present invention. An index-matching material 29 is used to minimize refraction caused by the adhesive layer. The surfaces should be closely index-matched as air gaps in between the lens surfaces can induce power and reduce the overall transmission due to reflection. Unmatched surfaces will also reduce the lamination strength, as there is less contact area for the adhesive. Edges 41 (all around lens 20) are sealed with index-matched material 29, such as urethane for protection, if needed.

Therefore in accordance with the present invention, the curvature of cap 25 relative to lens 21 is maintained to provide power such that the entire lens assembly 20 has substantially zero power and to maintain optical density (transmission) through the lens assembly 20. By providing power to cap 25, index of refraction differences through lens 20 are accounted for to reduce internal reflections, which reduce the transmission of visible light through the lens 20.

In addition, curvature of the entire lens assembly 20, as a whole, provides interchangeability between goggles (system 10) and spectacles (systems 100 and 200) as illustrated in FIG. 10. To achieve this, lens 20 provides sufficient wraparound or side protection for spectacles while being planar enough to be employed in goggles. In addition, lens 20 maintains an optical density, minimizes distortion, haze and other detrimental optical effects.

Light travels through solids slower then it does when traveling through air. This, in tandem with a curved lens, causes the light to be bent causing power to be induced through a lens. A plano lens has very little optical power (zero-power for cylinder or sphere lens) induced into the lens. This means to the human eye there is little difference between looking through the lens (with the exception of reflected or absorbed light reducing the transmission received to the eye) and the naked eye. With a spherical lens, zero-power is accomplished by varying the optical centers of a lens surface and varying the radius of the lens from these centers.

When a second lens element is added to a plano optic, if both of these lens designs were plano before being laminated, the resulting laminate would have power induced to it due to the laminate structure. In other words, altering the overall thickness of the laminate structure or material (i.e., density) or altering the radius of curvature of either lens results in power being induced into the laminate lens structure. To compensate for this effect, in accordance with the present invention, one or both of the lenses are designed with power so as to reflect the light such that the resulting lens laminate still remains plano (e.g., substantially zero power). This is more complex than just providing a standalone plano device, because the cumulative effect needs to be taken into consideration.

Referring again to FIG. 5, in accordance with the present invention, depending on the particular configuration, lens 25 may be employed as a cover lens and may not be needed for the lens assembly 20 (for example, if only ballistic protection is needed). In this instance, lens 21 is a ballistic lens and is preferably of zero-power. In other instances, both lens 21 and lens 25 may be used together.

Advantageously, the combination or sandwich of lenses is designed to also have zero-power. In other words, lens 21 is zero-power alone, and the lens assembly 20 as a whole is also zero-power. This may be provided by designing lens 25 to have non-zero power to compensate for any power effects induced by employing the laminate structure of lens assembly 20. In alternate embodiments, the structure of lens 25 may include a combination of lenses. One of the lenses in the combination may include a duplicate of lens 21 and an additional lens (not shown) to form lens 25. The additional lens would therefore include a radius of curvature, thickness and/or material to compensate for non-zero power throughout the entire lens assembly 20.

Therefore, assembly 20, when constructed, has substantially zero-power when employed by a user. In this way, the lens assembly provides protection to the user from one or more threats to ensure that little difference exists between looking through the lens assembly (with the exception of reflected or absorbed light reducing the transmission received to the eye) and the naked eye.

Zero-power lens structures are particularly useful in applications where depth perception must be maintained. For example, in military operations where the user must aim a weapon with eye gear on or spot a position with eye gear on, accuracy is important.

Although providing particular curvatures to the individual base lenses is difficult, initially in design, the product lens provided in accordance with the present invention permits a high degree of flexibility. Ballistic lens 25 alone may be clear, tinted and may include a dielectric stack having zero power, or lens assembly 20, which includes lens 25, may be employed with zero-power and provide laser protection and/or other optical features as described above. Other combinations of features and lens are also contemplated.

Haze can be a problem with holograms; therefore special care has been taken by the inventors in the creation of the mold surfaces, curves and lens coatings to minimize the haze present in the base polycarbonate lenses. With careful attention to production processes the inventors have been able to reduce the haze to less than 0.4%. Another problem with the visibly reflective holograms is a problem called narcissus, which means the user sees the reflection of their eyes in the lens surface. This is because the holograms reflect back certain wavelengths in the visible spectrum. This problem may be solved using a small amount of organic absorber dyes, which provide a predetermined optical density (OD) to provide protection. Absorber dyes may include metalloporphyrins, metallo-phthalocyanines, aza-variants of these, annellated variants of these, squaryliums, croconiums, aminiums, diimoniums, cyanines, etc. (L-1 dye). Other suitable dyes may also be employed. In one embodiment, the dye absorbs the reflected light and reduces the narcissus effect observed to acceptable levels. It also helps to provide protection against high angle incidence laser light as holograms only provide certain cones of protection and therefore are limited on the available angular protection. Dyes may be added for other purposes as well. For example, a dye may be added to lens 20 to provide support for a DE stack. The use of such dyes increase the adherence of a DE stack or other components formed on lens 20.

Therefore, the present invention includes lens and eye protection systems, which protect critical technologies from weather, chemical exposure and scratching while permitting a stable and robust platform for attachment of multiple laser protective technologies (DE stacks, holograms, organic absorber dyes, and polycarbonate (rugates, non-linear optics and specialized glass lens materials may also be used in this construct)). The lens is also capable of being worn and interchanged between a goggle and a spectacle and includes necessary optical, ballistic, field of view, transmissive/technologies.

One of the most difficult aspects for the present invention was maximizing the visible transmission of the device, while still providing necessary levels of protection. The more visible light attenuated, the more undesirable the transmission is to the wearer. In one embodiment of the present invention, a laser lens (e.g., in lens 20) is included which protects against both tunable and agile laser systems in both the visible and near infrared region of the electromagnetic spectrum. This lens is a careful combination of various laser protective technologies as described previously. The illustrative embodiment being described provides protection against over 400 nm of specific wavelengths of light in these regions. The photopic transmission of this device exceeded 35% and exceeds 45% in other preferred embodiments. Note, a normal sunshade lens found in commercially available sunglasses has a photopic luminous transmission of only 12–18%. Surprisingly, the laser lens created provides filtering protection three orders of magnitude greater than a sunshade lens at the specific wavelengths required, while possessing twice the photopic transmission, and still meeting ANSI Z87.1, ballistic and other important requirements described.

Having described preferred embodiments for eye protection systems (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A lens system for protection against laser light, and ballistics comprising:
   a first polymer lens having a convex surface and a non-zero power;
   two or more spectrally select filters, including a laser light filter;
   a second polymer lens having a concave surface;
   one of said filters comprising a dye disposed within one of the lenses;
   said filters further comprising one or more laminates selectively disposed on said convex or concave surfaces; and
   an adhesive for adhering the lenses together with the convex surface facing the concave surface to protectively sandwich the one or more laminates therebetween and to provide ballistics protection;
   wherein said second polymer lens having a non-zero power that compensates for power effects induced by the one or more laminates, so that during use the lens system has a substantially zero power.

2. The lens system as recited in claim 1, wherein said one or more laminates comprise:
   a hologram disposed on said convex surface; and
   a dielectric stack disposed on said concave surface.

3. The lens system as recited in claim 2, wherein said hologram provides protection from laser light.

4. The lens system as recited in claim 2, wherein the dielectric stack includes organic dielectrics.

5. The lens system as recited in claim 2, wherein the dielectric stack includes inorganic dielectrics.

6. The lens system as recited in claim 2, wherein the dielectric stack includes a rugate structure.

7. The lens system as recited in claim 2, wherein the adhesive seals edges of the first lens and second lens to protect the hologram and the dielectric stack.

8. The lens system as recited in claim 1, wherein the first lens and the second lens are formed from polycarbonate.

9. The lens system as recited in claim 1, wherein the laser light filter is selected from the group consisting of an absorber dye filter, an interference filter and a reflection filter.

10. The lens system as recited in claim 1, wherein photopic transmission of the lens exceeds 35%.

11. The lens system as recited in claim 1, wherein the first lens provides ballistic protection.

12. The lens system as recited in claim 1, wherein the lens system provides ballistic protection in accordance with MIL-STD-662E.

13. The lens system as recited in claim 12, wherein the adhesive seals edges of the first lens and second lens to protect the laminate.

14. The lens system as recited in claim 13, wherein the curvature includes a radius of about 123 mm on a concave surface.

15. The lens system as recited in claim 1, wherein the adhesive comprises an index-matching adhesive.

16. The lens system as recited in claim 1, wherein the lens system includes a curvature such that the lens is interchangeable and is mountable in both a spectacles assembly and a goggles assembly.

17. The lens system as recited in claim 1, wherein the lens system includes two lobes for covering the eyes of a user and an arch formed in the lens system between the two lobes corresponding to a nosepiece, the lens system being continuous without holes or slots.

18. The lens system as recited in claim 1, wherein the lens system includes a dye to prevent reflections.

19. The lens system as recited in claim 1, wherein the lens system is adapted to protect against at least one of ultraviolet light and sunlight.

20. The lens system as recited in claim 1, wherein the lens system includes a dye to provide a non-linear optical transmission spectrum.

21. The lens system as recited in claim 1, wherein at least one of the first lens and the second lens is coated with an inorganic polymer.

* * * * *